(12) United States Patent
Lew

(10) Patent No.: US 7,582,620 B2
(45) Date of Patent: Sep. 1, 2009

(54) **USE OF MANNAN FROM *SACCHAROMYCES CEREVISIAE* FOR THE TREATMENT OF ASTHMA**

(75) Inventor: D. Betty Lew, Memphis, TN (US)

(73) Assignee: The University of Tennessee Foundation, Knoxville, TN (US)

( * ) Notice: Subject to any disclaimer, the term of this patent is extended or adjusted under 35 U.S.C. 154(b) by 359 days.

(21) Appl. No.: 10/962,785

(22) Filed: Oct. 12, 2004

(65) Prior Publication Data

US 2005/0085442 A1    Apr. 21, 2005

Related U.S. Application Data

(60) Provisional application No. 60/511,050, filed on Oct. 14, 2003.

(51) Int. Cl.
*A61K 31/715*    (2006.01)
(52) U.S. Cl. .......................................... 514/54
(58) Field of Classification Search ................... 514/54; 536/123.1
See application file for complete search history.

(56) References Cited

U.S. PATENT DOCUMENTS

2005/0085442 A1 *   4/2005   Lew ........................... 514/54

OTHER PUBLICATIONS

[R] Lew et al., "Mitogenic Effect of Lysomal Hydrolases on Bovine Tracheal Myocytes in Culture," Journal of Clinical Investigation, 88, 1969-1975 (Dec. 1991).*

(S) Asako et al., "Analysis of IgE Reactivities of Purified Allergens from *Candida albicans* and *Malassezia furfur* Among Patients with Atopic Dermatitis," Arerugi, 51(8), 615-621 (Aug. 2002): first entered STN on Oct. 29, 2002: only CAPLUS abstract supplied.*

(T) Tomasiak et al., "N-Acetyl-Beta-Hexosaminidase Activity in Asthma," International Achives in Allergy & Immunology, 146, 133-137 (2008); copy supplied by applicant.*

[R] Lew et al., "Mitogenic Effect of Lysomal Hydrolases on Bovine Tracheal Myocytes in Culture," Journal of Clinical Investigation, 88, 1969-1975 (Dec. 1991).*

(S) Asako et al., "Analysis of IgE Reactivities of Purified Allergens from *Candida albicans* and *Malassezia furfur* Among Patients with Atopic Dermatitis," Arerugi, 51(8), 615-621 (Aug. 2002): first entered STN on Oct. 29, 2002: see also CAPLUS abstract supplied.*

* cited by examiner

*Primary Examiner*—Lawrence E. Crane
(74) *Attorney, Agent, or Firm*—Benjamin Aaron Adler

(57) ABSTRACT

The present invention provides methods of using mannose receptor blocker to treat airway disease such as asthma. The present invention also provides methods for reducing smooth muscle mass in an individual having an airway disease.

9 Claims, 14 Drawing Sheets

```
huASMC-MR   258  acgtctcctcatttcagccatggactgcagggctgcctggaggcccaggcggggcagg   317
                 ||| ||||||||| |||||||||||||||||||||||||||||||||||||||||||
ENDO-180    249  acatcttcctcatcttcagccatggactgcagggctgcctggaggccccaggcgggcagg   303
             42   N  I  F  L  I  F  S  H  G  L  Q  G  C  L  E  A  Q  G  G  Q huASMC-MR  1638  ccatttgcaagaaggcaggccagctgagccaggggccgcgagggggaccatggctgcc   1697
                 ||||| |||||||||||||||||||||||||||||||||||||||||||||||||||
ENDO-180   1629  ccatctgcaagaaggcaggccagctgagccaggggccgcgagggaggaccatggctgcc   1688
            502   S  I  C  K  K  A  G  Q  L  S  Q  G  A  A  E  E  D  H  G  C huASMC-MR  2238  gggcctgcagggggctggggcgccagtgctgagcctggccagctacgaggaggagcact   2297
                 |||||||||||| |||||||||||||||||||||||||||||||||||||||||||
ENDO-180   2229  gggcctgccaggagctgcgggtgctgagcctgctgagcctggccagctacgaggaggagcact   2288
            702   G  A  C  Q  E  L  G  A  Q  L  L  S  L  A  S  Y  E  E  E  H huASMC-MR  2478  tccgagggctgtgcgggtgccgtgctggaccctggcctcccctgcagtggccatgcagtgcgaca   2537
                 ||||||||||||||||||||||||||||||||||||||||||||||||||||||||||||
ENDO-180   2469  tccgagggctgtgcgggtgctgaggtgctggaccctggcctcccctgcagtggccatgcagtgcgaca   2523
            782   I  R  G  C  A  V  L  D  L  A  S  L  Q  W  V  A  M  Q  C  D huASMC-MR  2658  acaactccacgtgggcgcaggcgcagcgcatctgcacgtggttccaggccgagctgacct   2717   SEQ ID NO: 1
                 |||| ||||||||||||||||||||||||||||||||||||||||||||||||||||
ENDO-180   2649  accactccacgtgggcgcaggcgcagcgcatctgcacgtggttccaggccgagctgacct   2708   SEQ ID NO: 2
            842   H  H  S  T  W  A  Q  R  I  C  T  W  F  Q  A  E  L  T          SEQ ID NO: 3
```

Fig. 1A

OVA

Mannan (300 mg) + OVA

SEQUENCE LISTING

```
<160> NUMBER OF SEQ ID NOS: 4

<210> SEQ ID NO 1
<211> LENGTH: 300
<212> TYPE: DNA
<213> ORGANISM: Artificial Sequence
<220> FEATURE:
<223> OTHER INFORMATION: cDNA of human ASM-MR

<400> SEQUENCE: 1
acgtcttcct cattttcagc catggactgc agggctgcct ggaggcccag         50
ggcgggcagg ccatttgcaa gaaggcaggc cagctgagcc aggggggccgc        100 cgaggggggac catggctgcc gggcctgcca ggggctgggg gcccagctgc        150
tgagcctggc cagctacgag gaggagcact tccgaggctg tgcggtgccg         200
```

```
gacctggcct ccctgcagtg ggtggccatg cagtgcgaca acaactccac          250
gtgggcgcag gcgcagcgca tctgcacgtg gttccaggcc gagctgacct          300

<210> SEQ ID NO 2
<211> LENGTH: 300
<212> TYPE: DNA
<213> ORGANISM: Artificial Sequence
<220> FEATURE:
<223> OTHER INFORMATION: Endo180

<400> SEQUENCE: 2
acatcttcct catcttcagc catggactgc agggctgcct ggaggcccag           50
ggcgggcagg ccatctgcaa gaaggcaggc cagctgagcc aggggccgc           100 cgaggaggac catggctgcc gggcctgcca ggagctgggg gcccagctgc          150
tgagcctggc cagctacgag gaggagcact tccgaggctg tgcggtgctg          200
gacctggcct ccctgcagtg ggtggccatg cagtgcgaca accactccac          250
gtgggcgcag gcgcagcgca tctgcacgtg gttccaggcc gagctgacct          300

<210> SEQ ID NO 3
<211> LENGTH: 100
<212> TYPE: PRT
<213> ORGANISM: Artificial Sequence
<220> FEATURE:
<223> OTHER INFORMATION: carbohydrate recognition domain
      of huASM-MR

<400> SEQUENCE: 3

Asn Ile Phe Leu Ile Phe Ser His Gly Leu Gln Gly Cys Leu Glu
                5                  10                  15

Ala Gln Gly Gly Gln Ser Ile Cys Lys Lys Ala Gly Gln Leu Ser
            20                  25                  30

Gln Gly Ala Ala Glu Glu Asp His Gly Cys Gly Ala Cys Gln Glu
            35                  40                  45

Leu Gly Ala Gln Leu Leu Ser Leu Ala Ser Tyr Glu Glu Glu His
            50                  55                  60

Ile Arg Gly Cys Ala Val Leu Asp Leu Ala Ser Leu Gln Trp Val
            65                  70                  75

Ala Met Gln Cys Asp His His Ser Thr Trp Ala Gln Ala Gln Arg
            80                  85                  90

Ile Cys Thr Trp Phe Gln Ala Glu Leu Thr
            95                 100

<210> SEQ ID NO 4
<211> LENGTH: 4
<212> TYPE: PRT
<213> ORGANISM: Artificial Sequence
<220> FEATURE:
<221> NAME/KEY: DOMAIN
<222> LOCATION: 2
<223> OTHER INFORMATION: glycosylation consensus sequence of CRD5
      of the huASM-MR; Xaa=any at pos 2

<400> SEQUENCE: 4

Asp Xaa Ser Thr
```

USE OF MANNAN FROM *SACCHAROMYCES CEREVISIAE* FOR THE TREATMENT OF ASTHMA

CROSS-REFERENCE TO RELATED APPLICATION

This non-provisional patent application, filed as U.S. Ser. No. 10/962,785 on Oct. 12, 2004, now published as US-2005-0085442-A1 on Apr. 21, 2005, claims benefit of provisional patent application U.S. Ser. No. 60/511,050, filed Oct. 14, 2003, now abandoned.

BACKGROUND OF THE INVENTION

1. Field of the Invention

This invention relates generally to the field of bronchotherapeutics. More specifically, this invention relates to treatment of airway diseases such as asthma.

2. Description of the Related Art

Asthma is a global problem with serious morbidity, mortality and economic burden. Treatment of asthma often requires toxic doses of adrenergic bronchodilators and steroids. An increase in bronchial smooth muscle mass due to hypertrophy and hyperplasia is an important element of airway structural changes, the remodeling process occurring in asthma. The increase in bronchial smooth muscle mass may play a critical role in the development of airway hyper-reactivity (AHR), the hallmark of asthma. However, the pathogenesis of bronchial smooth muscle hyperplasia/hypertrophy is not well understood, despite the knowledge in this area disclosed over the last decade.

Airway inflammation is a key feature of asthma. Of the inflammatory mediators associated with asthma, histamine, lysosomal hydrolases, endothelin-1, thromboxane, and tryptase have been reported to directly stimulate airway smooth muscle cells proliferation. In addition, smooth muscle cells with asthma phenotype can produce a number of growth factors and cytokines that may contribute to the inflammatory process and airway hyper-reactivity. Finally, airway remodeling, including airway smooth muscle cells proliferation, has been shown to correlate with airway responsiveness.

Lysosomal Hydrolases

The mitogenic function of lysosomal hydrolases in airway smooth muscle cells has been studied. Lysosomal hydrolases are produced and secreted by inflammatory cells, i.e., mast cells, macrophages, neutrophils, and eosinophils, in response to various soluble and particulate stimuli such as antigen bound to IgE antibody, β-glucan and zymosan. These protease-resistant lysosomal hydrolases are important putative mediators responsible for airway smooth muscle cell proliferation occurring in asthma. Increased levels of these enzymes in bronchoalveolar lavage fluid are associated with experimentally induced asthma in humans and guinea pigs.

Lysosomal hydrolases are often used as inflammatory markers. Moreover, it has been shown that leukotrienes, LTB4 and LTC4, augment the synthesis and secretion of hexosaminidases in macrophages. It has been shown that lysosomal hydrolases (β-hexosaminidases (Hex A, Hex B) and β-glucuronidase) and mannosylated human or bovine serum albumin stimulate proliferation of bovine tracheal myocytes. At physiologically and pathologically relevant concentrations, Hex A and Hex B stimulate DNA synthesis and increase cell number.

The mitogenic action of purified human placental b hexosaminidases is mediated by 175 kD mannose recognizing receptors (ASM-MR) which share structural, topological, and functional properties with macrophage mannose receptor (Mø-MR). A monoclonal antibody (mAb15) directed to the extracellular domain of Mø-MR acts as an agonistic antibody for DNA synthesis. Unlike most glycoproteins and membrane glycoconjugates of the majority of higher organisms, lysosomal hydrolases possess high mannose chains as a remnant of the mannose-phosphate targeting marker. Lysosomal hydrolases are thus taken up by either mannose receptor or cation independent mannose-6-phosphate ($MPR^{CI}$/IGF-II) receptor.

Mannose Recognizing Receptors

Macrophage mannose receptor (Mø-MR) is the first recognized member of a growing family of mutilectin receptor proteins involved in molecular scavenging of glycoconjugates with terminal mannose, N-acetylglucosamine or fucose. It has specialized high affinity binding sites involved in a pattern recognition and host defense against pathogens such as *Pneumocystis carinii, Mycobacterium tuberculosis, Candida albicans*, and *Leishmania donovani*. Other members of mannose receptor family are secretory phospholipase $A_2$ receptor, DEC205, and Endo180. Endo180 is an endocytic $Ca^{++}$-dependent lectin receptor expressed in fibroblasts, endothelial cells and macrophages.

Airway smooth muscle cells express mannose receptors (ASM-MR). While ASM-MR and Mø-MR bind to mannose affinity columns, Endo180 binds to N-acetylglucosamine affinity matrix but not mannose affinity column. However, Endo180 recognizes mannose residues by the second domain of carbohydrate recognition domain (CRD) that is a low affinity binding domain. Each of these receptors mediates endocytosis, but physiological ligands have only been identified for Mø-MR, ASM-MR and secretory phospholipase A2 (sPLA2) receptor. Indeed, sPLA2 receptor and dendritic cell receptor DEC205 do not contain the conserved residues necessary for $Ca^{++}$-dependent sugar binding.

The features and functions of individual domains of macrophage mannose receptor have been studied extensively. The N-terminal cysteine-rich domain contains N-acetylgalactosamine 4-sulphate binding site involved in recognition of leutropin. No specific function of fibronectin type II (FN II) repeat domain of Mø-MR has been determined. In other proteins containing FN II such as gelatinases and possibly in fibronectin, these domains are involved in binding of gelatin. Of the carbohydrate recognition domains (CRD) of Mø-MR, CRD4-5 form a protease-resistant ligand-binding core essential for high affinity binding of mutivalent ligands. However, maximum affinity for yeast mannan is achieved when CRD4-8 are intact. The cytoplasmic domain of Mø-MR contains a di-aromatic motif, $Tyr^{18}$-$Phe^{19}$, which is important in endosomal sorting.

Among the mannose receptor family members, airway smooth muscle cell mannose receptor (ASMC-MR) has unique mitogenic function (Table 1). Unique ligand binding property of the ASM-MR may have evolved in order to bind mannosyl-rich lysosomal hydrolases released from lung mast cells and macrophages in direct contact with bronchial smooth muscle.

ASMC-MR mitogenic activation is accompanied by a transient elevation of cyclic adenosine monophosphate (cAMP), activation of protein kinase C (PKC) and p21Ras- and PKC-dependent activation of p44/42MAPK. The onset of p44/42MAPK activation in response to the ASM-MR activation is late (30 min) and the activation lasts for 4 hours. This sustained activation of p44/42MAPK is considered an important signal to cause cell proliferation.

While the main treatment of asthma therapy, i.e., inhaled corticosteroids, effectively reduces inflammation and remodeling of epithelium and basement membrane, no agents have been proven effective in reducing smooth muscle mass in asthmatic patients. Mannan is a carbohydrate cell wall component of yeast such as *Saccharomyces cerevisiae* and is a mannose receptor blocker. The mannan component of microbial cell wall renders pattern recognition by host cellular receptors and serves as a virulence factor for the organism by supporting differentiation and protecting from starvation and/or stress conditions. The inventors recognize that pathological airway smooth muscle cells proliferation may be controlled by blocking airway smooth muscle cells mannose receptor (ASMC-MR) with mannan or other anti-asthma drugs having airway smooth muscle cells mannose receptor ligand structural or functional properties.

There is a need in the art for improved methods of therapy to treat asthma by blocking the onset of airway smooth muscle cells proliferation and the resultant airway hyperreactivity. The prior art is deficient in the lack of drugs to specifically block mannose receptors on airway smooth muscle cells and of methods to treat asthma using these blockers. Specifically, the prior art is deficient in methods of using mannan as a therapeutic in the treatment of asthma. The present invention fulfills this longstanding need and desire in the art.

lowing description of the presently preferred embodiments of the invention given for the purpose of disclosure.

BRIEF DESCRIPTION OF THE DRAWINGS

FIGS. 1A-1B identify the cDNA sequence of huASM-MR (FIG. 1A) and depict the primary structure of huASM-MR (FIG. 1B).

FIGS. 3A-3B show H & E staining of sections taken mid-trachea for infusions of 1 mg/200 μl Hex and 5% glycerol in saline control. FIGS. 3C-3D show scanning electron micrographs of sections taken mid-trachea for 1 mg/200 μl Hex and 5% glycerol in saline control. FIG. 3E is a higher magnification of the trachealis muscle area marked by an arrow. Sm, smooth muscle; C, cartilage FIG. 4 demonstrates that aerosolized b hexosaminidases (Hex) increases airway hyperreactivity in naive wild type FVB/N mice. Results are mean Penh (% of baseline) at a Mch concentration 25 mg/ml±SEM (n=3). * denotes value significantly different from the value obtained with vehicle control.

TABLE 1

Comparison of the Properties of Mannose Receptor Family Members

| Receptor | MøMR | ASM-MR | Endo180 | sPLA2R | DEC205 |
|---|---|---|---|---|---|
| Mass (kD) | 165-180 | 175 | 180 | 180 | 205 |
| Amino acid Identity (%) | | 35 | 100 | 99 | 36 | 33 |
| Ca++ binding (Ctype) | Yes | Yes | Yes | No | No |
| Clathrin coated pits | Yes | Yes | Yes | Yes | Yes |
| Endogenous Ligand Known | Yes | Yes | Yes | Yes | No |
| Mannose binding | Yes | Yes | Yes | No | No |
| GlcNAc binding | Yes | Yes | Yes | No | No |
| kD (nM) | 10 | 50 | Unk | Unk | Unk |
| Function | Scavenge Host defense | Mitogenic | Osteogenic Collagen uptake | clear sPLA2 | present antigen |

SUMMARY OF THE INVENTION

The present invention provides a method of using a pharmacologically effective amount of mannose receptor blocker to treat an airway disease in an individual.

The present invention also provides a method of using a pharmacologically effective amount of mannan to treat asthma in an individual.

The present invention is directed further to a method for reducing smooth muscle mass in an individual with an airway disease by administering a pharmacologically effective amount of mannose receptor blocker to the individual.

The present invention is directed further still to a method for reducing smooth muscle mass in an individual with asthma by administering a pharmacologically effective amount of mannan to the individual.

Figure 5:
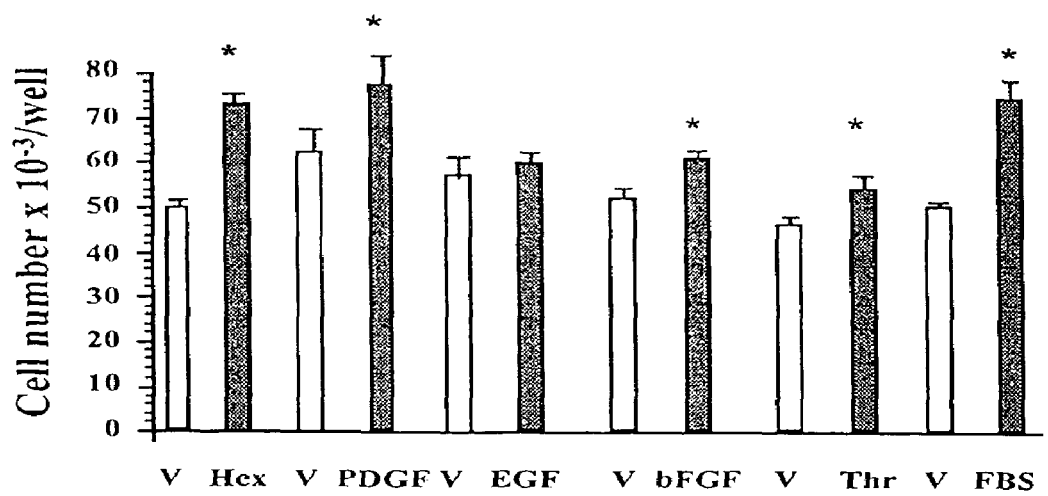

Other and further aspects, features, benefits, and advantages of the present invention will be apparent from the fol- FIG. 5 compares the effects of growth factors in human airway smooth muscle cells. Results are mean±SEM of triplicate cultures. *denotes value significantly different from the value obtained from the vehicle control.

Figure 6A:
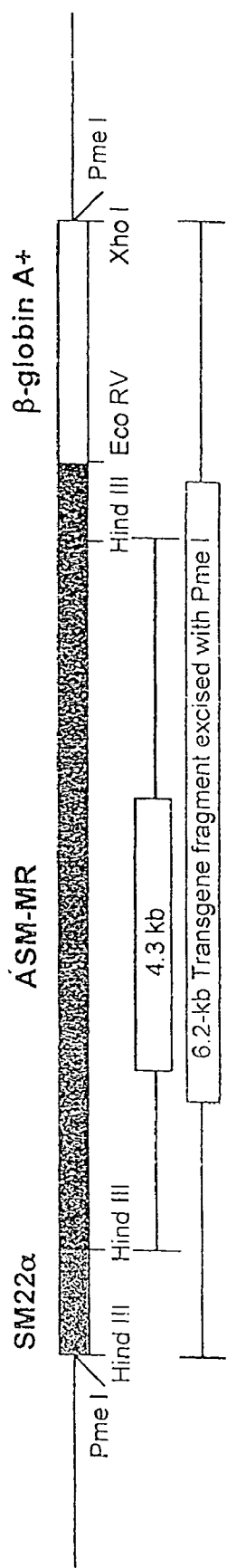
Figure 6B:
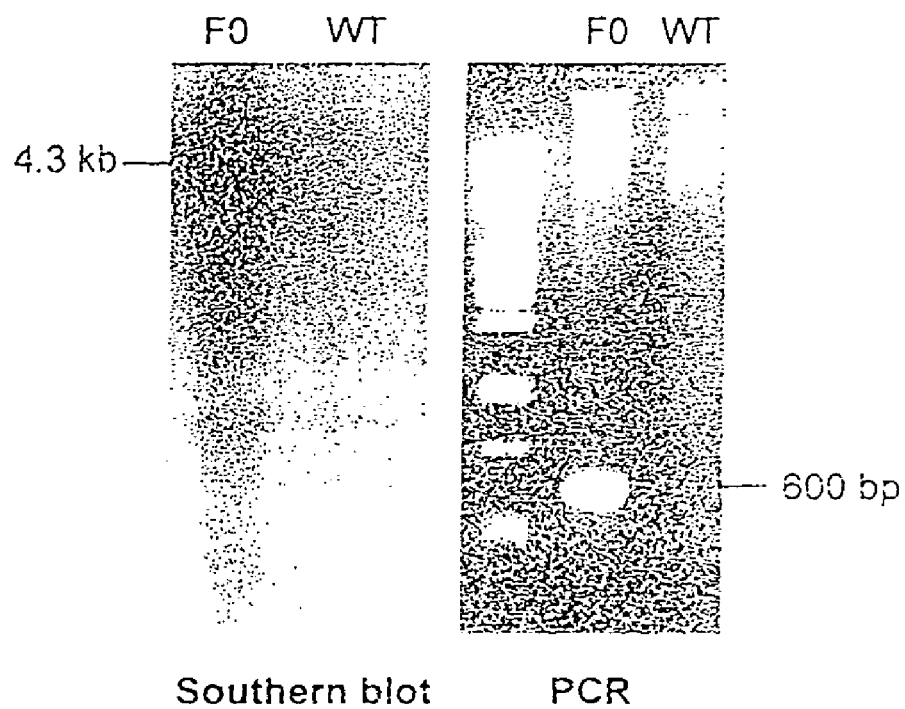

FIGS. 6A-6B depict the genotyping results of the Tg founder mice. FIG. 6A depicts the construction of the SM22 alpha/ASM-MR transgene. FIG. 6B is a southern blot confirming the transgenic founders.

Figure 7:
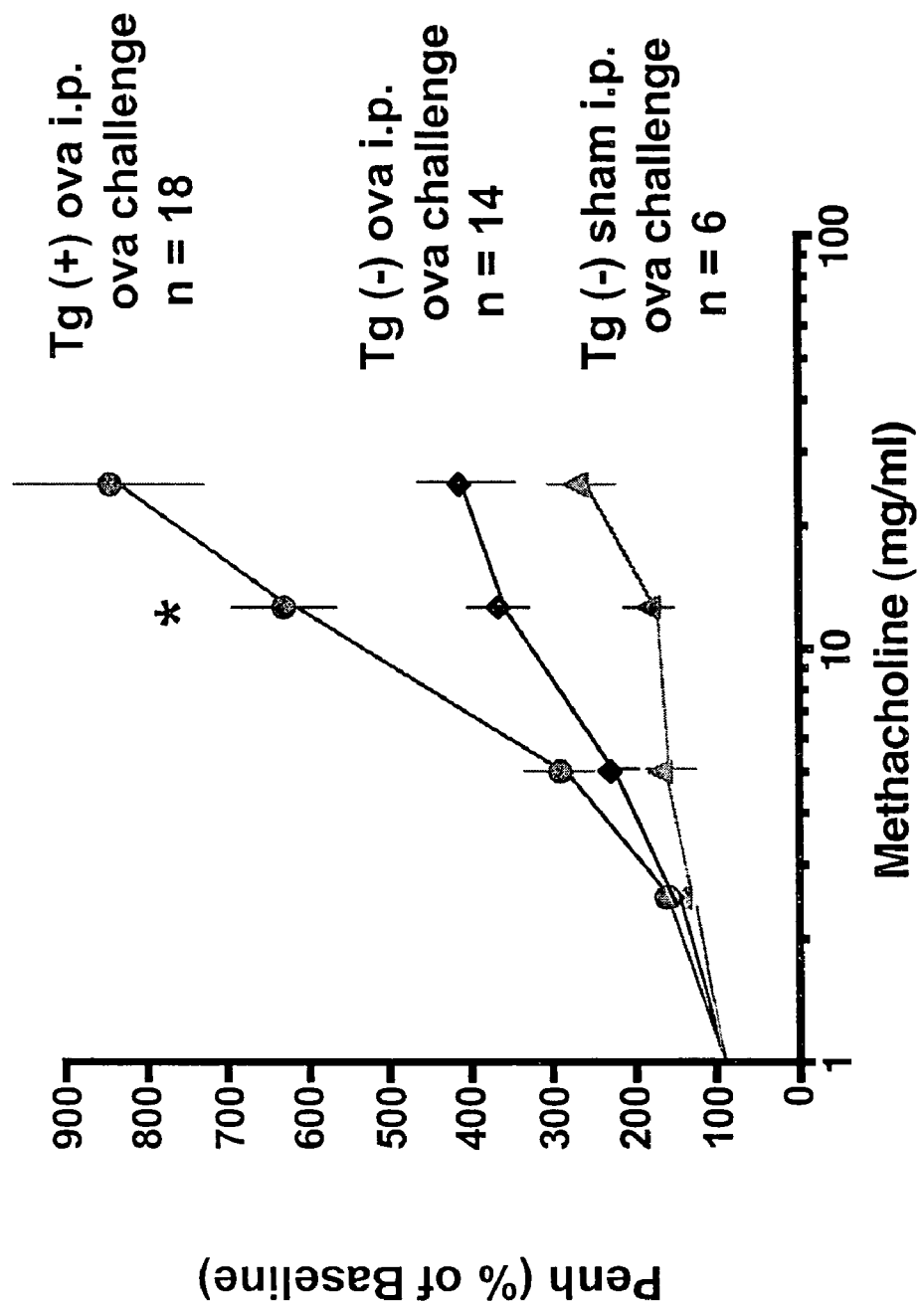

FIG. 7 demonstrates that overexpression of huASM-MR causes increase in airway hyperreactivity in allergic model of FVB/N mice.

Figure 8:
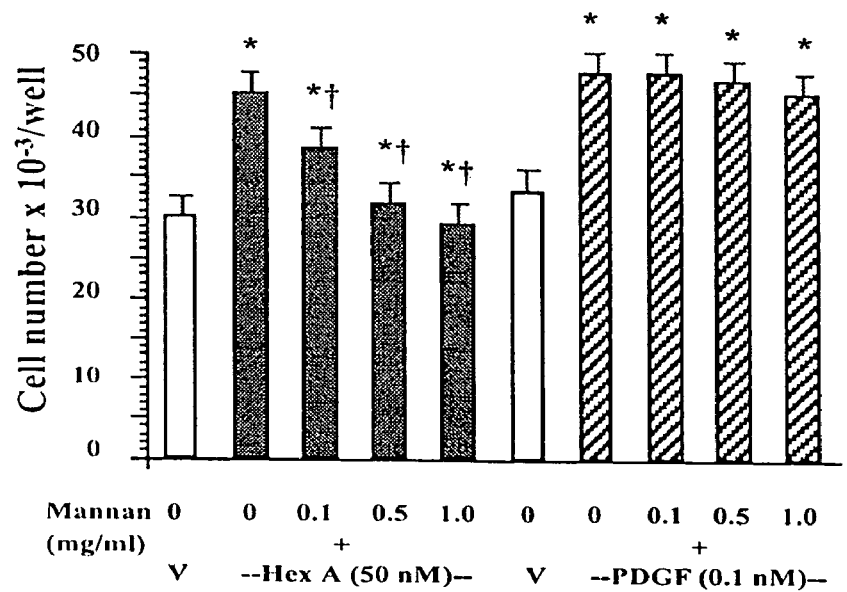

FIG. 8 demonstrates the effect of mannan on b hexosaminidases (Hex)- and PDGF-induced mitogenesis in human airway smooth muscle cells. Results are mean±SEM of triplicate cultures. *denotes value significantly different from the value obtained from the vehicle control. † denotes value significantly different from the value obtained from Hex stimulation alone.

Figure 9:
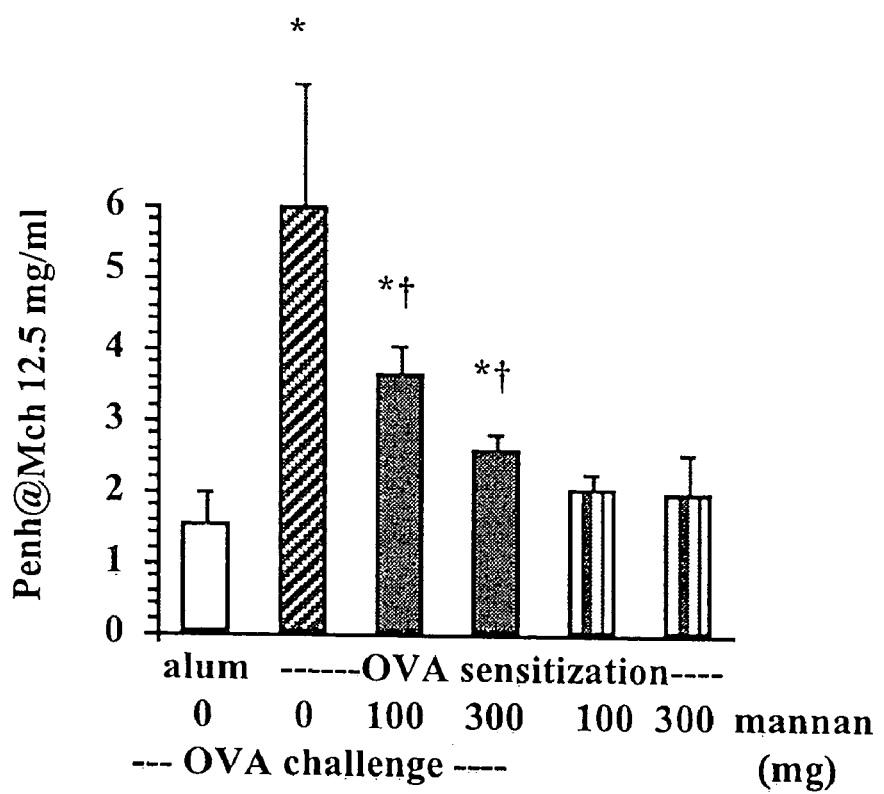

FIG. 9 demonstrates that aerosolized yeast mannan blocks airway hyperreactivity in OVA-sensitized murine allergic asthma model. Results are mean±SEM (n=3). * denotes value significantly different from that of non-immunized (alum only)- and OVA-challenged mice (open bar). † denotes value significantly different from that of OVA-sensitized and -challenged mice (hatched bar).

Figure 10B:
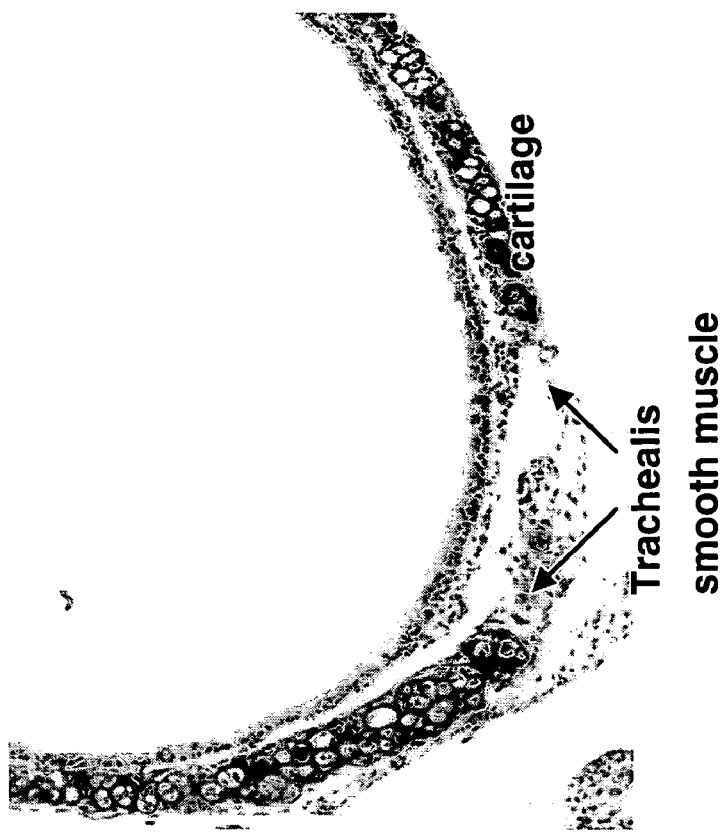
Figure 10A:

FIGS. 10A-B show mannan from *Saccharomyces cerevisiae* protects airway epithelium. FIG. 10A shows H&E staining of a cross section of trachea of an ovalbumin-sensitized and -challenged mouse on day 35. Epithelial layer was disrupted and tracheal smooth muscle was in a contractile state. FIG. 10B shows H&E staining of a cross section of trachea of mouse treated with aerosolized mannan (300 mg). Trachealis muscle has normal appearance and the epithelial layer is intact.

Figure 11:
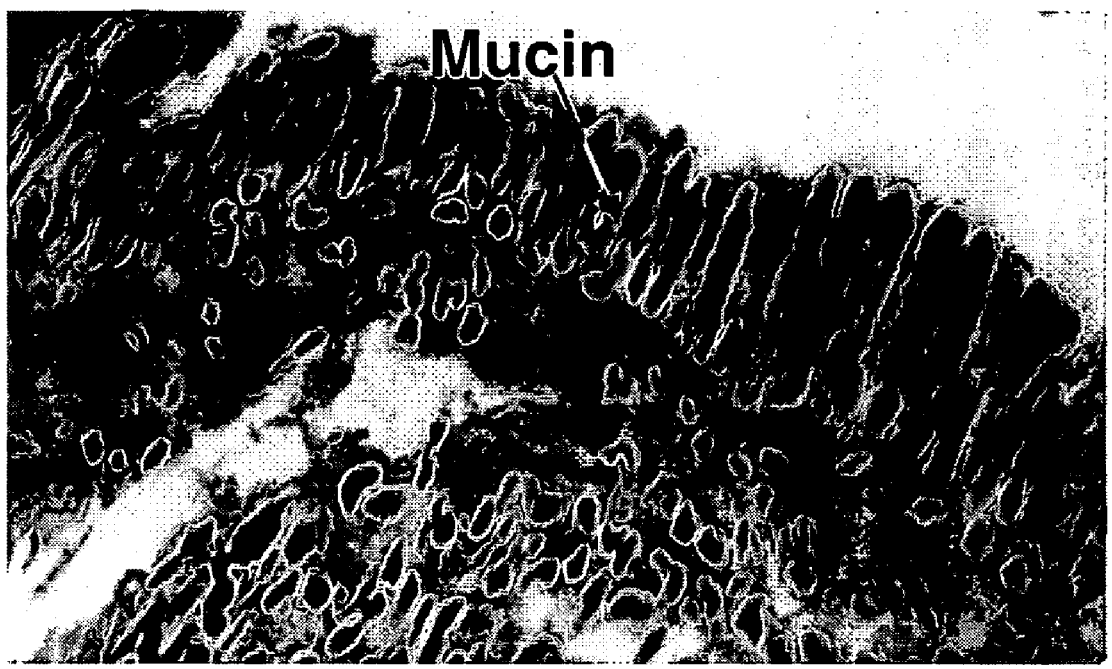

FIG. 11 shows a protective effect of *Saccharomyces cerevisiae* mannan on airway epithelium. The PAS stained sections from a mannan treated-mouse depicts mucin.

Figure 12A:
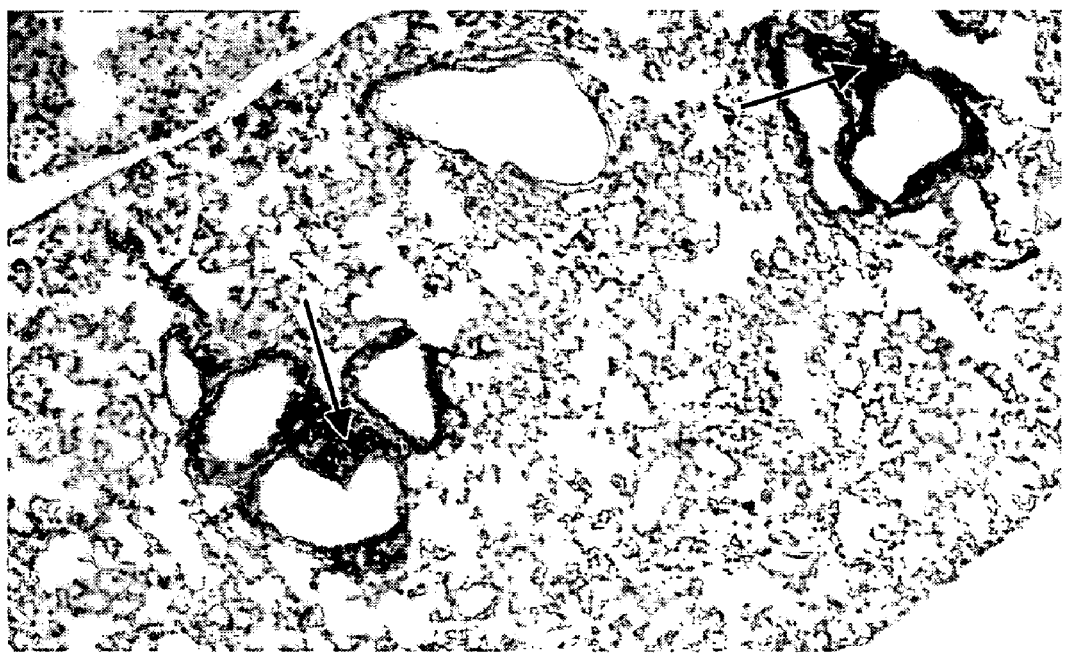
Figure 12B:
Figure 12C:
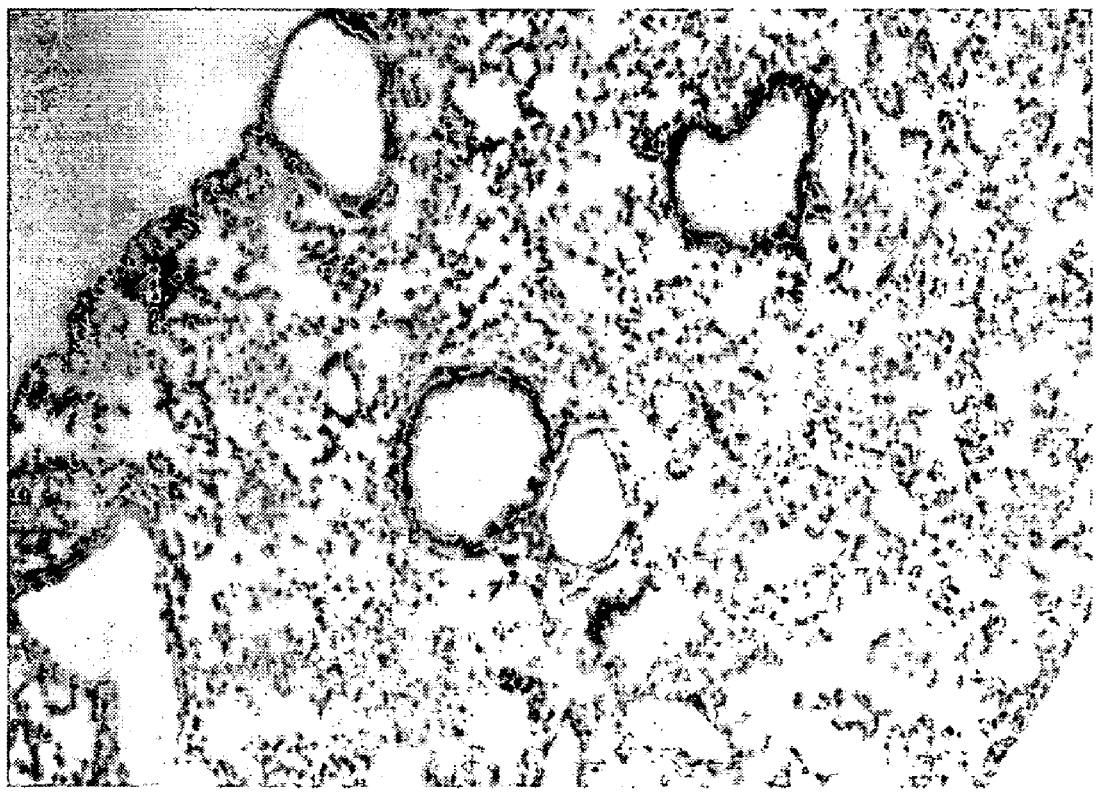

FIGS. 12A-C show inhibition of cellular infiltration by aerosolized mannan from *Saccharomyces cerevisiae*. FIGS. 12A-B show H&E sections of lung from an ovalbumin-sensitized and ovalbumin-challenged mouse. Peribronchiolar infiltration of cells can be identified as lymphoid infiltration under higher manification (FIG. 12B). FIG. 12C is a H&E section of a lung from mannan (300 mg) pretreated mouse. There was a marked decrease in peribronchiolar cellular infiltration in 3 out of 4 bronchioles.

DETAILED DESCRIPTION OF THE INVENTION

The following abbreviations are used herein: ASM or ASMC: airway smooth muscle or airway smooth muscle cell(s); MR: mannose receptor; AHR: airway hyperreactivity; ASMC-MR: airway smooth muscle cell mannose receptor; Hex A, Hex B: β hexosaminidases; FN: fibronectin; BPD: bronchopulmonary dysplasia; COPD: chronic obstructive pulmonary disease.

Provided herein is a method of treating airway diseases, such as asthma, by administering, e.g. via inhalation, an aerosolized blocker of mannose receptor on airway smooth muscle cells (ASMC-MR). An example of mannose receptor blocker is mannan which functions as a ligand for the mannose receptor on airway smooth muscle cells and thereby inhibits mitogenic activation of airway smooth muscle cells and the onset of airway hyperreactivity. Thus, methods of inhibiting onset of airway smooth muscle mass increase in an individual with an airway disease or with asthma are also provided. The methods disclosed herein further may provide a therapeutic effect against inflammation of the airway that occurs during asthma and other airway diseases. It is contemplated that airway diseases such as bronchopulmonary dysplasia (BPD) or chronic obstructive pulmonary disease (COPD) may be treated by these methods.

Mannan, a polymer of mannose, composes 45% of the cell wall of *Saccharomyces cerevisiae*. Other sources of mannan include Aloe vera, Konjac glucomannan, *Candida* and *Mycobacteria*. Mannan or other mannose receptor blocker can be used in the methods described herein as an adjunctive therapy to current medication. The methods of using mannan or other mannose receptor blocker as disclosed herein would also be useful to target airway remodeling, such as smooth muscle remodeling.

It is specifically contemplated that pharmaceutical compositions may be prepared using mannan or other compounds or drugs of the present invention. Pharmaceutical composition comprises mannan or other compounds or drugs and a pharmaceutically acceptable carrier. In one embodiment, mannan is delivered via aerosolization. Methods of aerosol delivery are standard in the art. Moreover, methods of delivering mannan or other mannose receptor blocker as a pharmaceutical composition in a suitable solvent, either wet or dry, are also standard in the art. It is further contemplated that mannan or other mannose receptor blocker may be administered by the patient at home as is common with other inhaled asthma medications.

As an in vivo therapeutic, the mannan or other mannose receptor blocker is administered to an individual, i.e, a patient or an animal, in therapeutically effective amounts. A therapeutically effective amount is one that reduces or eliminates the airway disease, such as asthma, or one or more components of the disease, such as, but not limited to, an increase in smooth muscle cell proliferation or smooth muscle mass, airway inflammation or airway hyperreactivity.

Although the dose and dosage regimen will depend upon, inter alia, the patient, the patient's history and other factors, a person having ordinary skill in this art would readily be able to determine, without undue experimentation, the appropriate dosages. The dosage or inhalation regimen may comprise one or more inhalation therapies per day using all or a divided daily dose over a period of time. It is also contemplated that a dosage or inhalation regimen may be repeated as necessary. The regimen will be continued to optimize effectiveness while balanced against any actual or potential negative effects of treatment. Again it is well within the purview of a skilled artisan to determine and design an inhalation regimen for a patient.

Mitogenic activation by airway smooth muscle cell mannose receptor (ASMC-MR) is unique to members of the mannose receptor family and is contemplated to be structurally based. ASMC-MR comprises at least the nucleotide sequence shown in SEQ ID NO: 1. While mannan is a known mannose receptor on airway smooth muscle cells blocker, it is contemplated that other blockers of mannose receptor may be useful in the treatment of airway diseases, e.g., asthma. The structure-function relationship of human mannose receptor on airway smooth muscle cells as characterized by, but not limited to, the sequence of SEQ ID NO: 1 may be used to develop other methods and compounds for the prevention of airway diseases, such as asthma. Specifically, it is contemplated that mannose receptor blockers may be designed based on the ligand binding properties and three-dimensional studies of human mannose receptor on airway smooth muscle cells such as those elucidated from the domains of human mannose receptor on airway smooth muscle cells essential for mitogenic function.

Additionally, it is contemplated that a tissue specific knock-out (ASM-MR−/−) murine model system can be used to examine signal transduction pathways involved in mannose receptor on airway smooth muscle cells activation, such as, but not limited to, activation of $p44/42^{MAPK}$ or $\alpha 5\beta 1$ integrin and FN expression. It is further contemplated that compounds capable of blocking these pathways may provide a therapeutic benefit in preventing the onset of airway smooth muscle cell proliferation and airway hyper-reactivity as evidenced in asthma or other airway diseases.

Thus, the present invention provides a method for treating an airway disease in an individual by administering a pharmacologically effective amount of an aerosolized mannose receptor blocker to the individual. In one embodiment, the mannose receptor blocker is yeast-derived mannan and the mannose receptor may be an airway smooth muscle cell mannose receptor. The mannose receptor on airway smooth muscle cells may comprise the nucleotide sequence of SEQ ID NO: 1. Furthermore, blocking mannose receptor would inhibit the onset of airway smooth muscle cell proliferation and/or airway hyperreactivity. Representative examples of airway diseases include, but are not limited to, asthma, bronchpulmonary dysplasia and chronic obstructive pulmonary disease. In general, aerosolized mannose receptor blocker can be administered via a nebulizer or via an inhaler.

In a related embodiment of the present invention, there is provided a method for reducing smooth muscle mass in an individual with an airway disease comprising administering a pharmacologically effective amount of an aerosolized mannose receptor blocker to the individual. The mannose receptor blockers, the mannose receptors, the airway diseases and the method of administering the mannose receptor blockers are as described supra.

In another embodiment of the present invention, there is provided a method for treating asthma in an individual comprising administering a pharmacologically effective amount of an aerosolized mannan to the individual. In this embodiment mannan acts as a mannose receptor blocker. Blocking mannose receptor inhibits onset of airway smooth muscle cell proliferation, as well as prevents inflammation of airway and/or airway hyperreactivity. In all aspects of this embodiment, mannose receptors and the method of administering the mannan are as described supra.

In an embodiment related to this method for treating asthma, there is provided a method of reducing smooth muscle mass in an individual with asthma comprising administering a pharmacologically effective dose of an aerosolized mannan to the individual. In all aspects of this embodiment, mannose receptors and the method of administering the mannan are as described supra.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Experimental Protocols And Reagents

Assessment of Cell Proliferation

Measurement of $^3$H-thymidine incorporation as an assessment of the rate of DNA synthesis is performed as described previously (Lew et al., 1994) with a modification. After the cells reach confluency and contact-inhibited in microtiter wells (16 mm wells for human airway smooth muscle cells), the medium is replaced with medium M199 (Cellgro, Mediatech, Washington D.C.) or SmBM (for huASMC) containing 0.1% vol/vol fetal bovine serum (FBS, Hyclone Lab. Inc., Logan, Utah) 48 h before exposure to test substances. $^3$H-thymidine (0.5 μCi/well or 2.5 μC/16 mm well, sp act 10 Ci/mmol, Amersham Corp., Arlington Heights, Ill.) is added to the cells 18 h after the addition of test substances and cells are harvested 18 h later. Radioactivity is quantified in a liquid scintillation counter (2000 CA; Packard Instrument Co., Downers Grove, Ill.). Experiments are performed in quadruplicate and repeated 3 times.

Cell Counting

Cell counts and cytotoxicity are assessed by tetrazolium salt reduction (MTT) calorimetric assay in parallel experiments. Millipore filtered MTT (5 mg/ml, Sigma Chemical Co., St Louis, Mo.) dissolved in phosphate buffered saline (PBS, pH 7.2) is added to the microtiter wells (10 μl/well, 20 μl/16 mm well) at the end of the experimental period. After incubating at 37° C. for 4 h, media is removed from the microtiter wells and acidified with 0.04 M HCl. 2-propane/isopropanol is added to the wells at 200 μl/well or 400 μl/16 mm well for human airway smooth muscle cells. The plates are left at room temperature for 30 min and optical density is obtained by an ELISA reader (EL340 Microplate, Bio-Tek instruments, Winooski, Vt.) at 570 nm wave length. The results obtained by MTT assay correlate well with the viable cell counts obtained by the Trypan blue method using hemocytometer (Sigma cell count instruction manual). Cytotoxicity also is measured by LDH assays (Sigma). Release of LDH greater than 5% is considered cytotoxic.

Western Blot Analysis of ASM-MR

Proteins in cell lysates are separated by 10% SDS-PAGE and transferred onto a nitrocellulose membrane. Membranes are blotted with a cross-reacting monoclonal antibody (mAb15-2-2 at 1 μg/ml) directed to Mø-MR (TNO, Leiden, Netherlands) or with a custom made polyclonal antibody directed against the $Asn^{843}$-containing region of huASM-MR at 1:2000 dilution (Rockland Immunochemicals Inc., Boyertown, Pa.). Protein bands are detected by ECL system (Amersham).

RNA and DNA Blotting Analysis

Total RNA is purified using TRIzol reagent (Gibco Life Technologies). RNAs are run on 1% agarose gel containing 2.2 M formaldehyde and then transferred onto a nylon membrane. A calf thymus genomic DNA blot is prepared by conventional methods. After cross-linking of DNA or RNA onto the membrane by ultraviolet light irradiation, hybridization is performed. The hybridization signals are detected by autoradiography with Kodak O-Mat x-ray film using intensifying screens at −70° C.

Protein Measurement by BCA Method

BCA protein assay reagents (Pierce) are used to measure protein following the manufacturer's instruction.

b Hexosaminidase A b hexosaminidase A (Sigma Chemical Co., St Louis, Mo.) is dialyzed against phosphate buffered saline (PBS) for 2 h using Slide-A-Lyzer (M.W. cut-off: 10,000, Pierce, Rockford, Ill.) and concentrated by centrifugation using Microcon 50 (M.W. cut-off: 50,000, Millipore). The endotoxin level at working concentration of Hex is <0.2 EU/ml.

b Hexosaminidase (Hex) Assay

The activities of Hex are determined as previously described (Lew et al., 1991). Samples (50 μl) are incubated with 100 μl of pre-warmed buffered substrate (5 mM p-nitrophenyl-2-deoxy-β-D-glucosaminide in 0.1 M citrate/phoshate buffer, pH 4.5) in 96-well microtirter plates for 1 h at 37° C. After incubation, the reactions are stopped by the addition of 100 μl of 0.5 M boric acid/NaOH buffer, pH 10.6. p-nitrophenol released by the hydrolytic activity is quantified spectrophotometrically by using a Biotek ELISA reader at 405 nm wave length. The Beer-Lambert Law and molecular extinction coefficient for p-nitrophenol (E=18,700) are applied to obtain units of specific activity expressed as micromoles of substrate cleaved/h/$10^6$ cells. Purified Hex (Sigma) is tested in each assay as a positive internal control.

Histopathology and Immunohistology Mice are sacrificed after the broncho alveolar lavage procedure for histopathology of smooth muscle containing organs: lung, heart, intestine, uterus, and vessels. An α-smooth muscle isoactin histo staining kit (Sigma) is used to stain smooth muscle in antigen-retrieved paraffin-embedded sections according to the manufacturer's instructions. Primary mouse monoclonal antibody (clone 1A4) was developed against the N-terminal synthetic decapeptide of α-smooth muscle actin. This antibody is specific for α-smooth muscle actin and cross reacts with mouse, rat, rabbit, guinea pig, bovine, and human antigen. The second antibody is biotinylated and uses ExtrAvidin-peroxidase reagent.

Mannan

Mannan from *Saccharomyces cerevisiae* (Sigma-Aldrich) is dissolved in endotoxin-free deionized $dH_2O$ or diluted in sterile normal saline to achieve physiologic osmolarity, i.e., 280 mOsmol/l. The solution is sterilized and purified by filtering through 0.22 μm high protein binding membrane (Millipore) to remove any trace of protein Limulus Amebocyte Lysate (LAL) Assay Quantitative chromogenic LAL kit (QCL-1000, Biowhittaker, A Cambrex Co., Walkersville, Md.) is used according to the manufacturer's protocol including inhibition or enhancement test with spiked samples. The principle of the assay system is that endotoxin catalyzes proenzyme to enzyme in LAL. The initial rate of activation correlates with the concentration of endotoxin. The activated enzyme then cleaves pNA from the colorless substrate Ac-Ile-Glu-Ala-Arg-pNA. The pNA released is measured photometrically at 405 nm wave length. Endotoxin levels are derived from standard curves and expressed in EU/ml (1 EU=0.1 ng).

Statistical Analysis

Data are analyzed by STAT-VIEW 4.5 and SuperANOVA software systems (Abacus concepts, Berkeley, Calif.) with Dunnett's post hoc tests. A P value of less than 0.05 is considered statistically significant. Data are expressed as Mean±SEM. For lung histology and morphometry, the method of Leigh et al. (2002) is used to analyze the α-smooth muscle isoactin stained areas. A software IP Lab version 3.5 (Scanalytics, Inc.) is used for morphometric analysis.

EXAMPLE 1

Characterization of Airway Smooth Muscle Cell Mannose Receptor (ASMC-MR)

Human mannose receptor on airway smooth muscle cells was cloned from mRNA isolated from human bronchial ASM cells by RT-PCR using primers designed based on the most recently published sequence of Endo180 cDNA (Sheikh et al., 2000). Preliminary cloning and sequencing information of the full-length cDNA of human ASM-MR (SEQ ID NO: 1) showed 99% identity to that of an uncharacterized 5,641 bp EST clone (KIAA0709) isolated from a human adult brain. The coding region of this EST clone (KIAA0709) is identical to that of the Endo180 (4,639 bp) (SEQ ID NO: 2) except for one amino acid, i.e., $Val^{43}$ versus $Ile^{43}$, and differs by four amino acids in carbohydrate recognition domains (CRDs) (SEQ ID NO: 3) from huASM-MR (FIG. 1A).

Figure 1B:
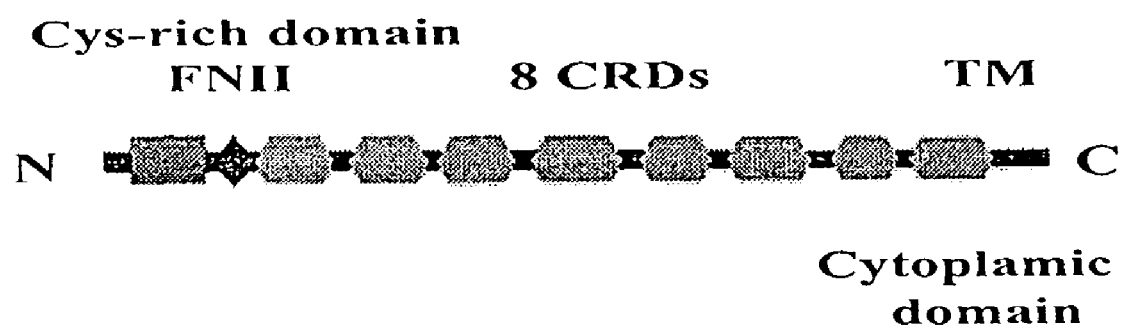

The primary structure of mannose receptor on airway smooth muscle cells is identical to Endo180 and includes an amino-terminal cysteine-rich domain, a fibronectin type II domain, eight CRDs, a transmembrane domain and a cytoplasmic carboxy-terminal domain (FIG. 1B). The coding region of huASMC-MR differs from that of Endo 180 by 7 nucleotides and 5 amino acids. The amino acid at position 843 in CRD5 of the huASM-MR is Asn compared to His in Endo180. This difference is likely an important feature as the Asn residue of huASM-MR is followed by Serine and Threonine, indicating the glycosylation consensus sequence Asn-X-Ser/Thr (SEQ ID NO: 4). In the case of IL-2, substitution of a single amino acid at the carbohydrate recognition site ($Asn^{26}$ to $Gln^{26}$ or $Asp^{26}$) affected the binding of mannose-type glycan on IL-2Rα and cell proliferation activities, perhaps due to the failure of high affinity heterooctamer complex formation. Therefore, the $Asn^{843}$ residue of mannose receptor on human airway smooth muscle cells may account for the specific affinity to endogenous mannosyl-rich ligands such as b hexosaminidase.

EXAMPLE 2

Figure 2A:
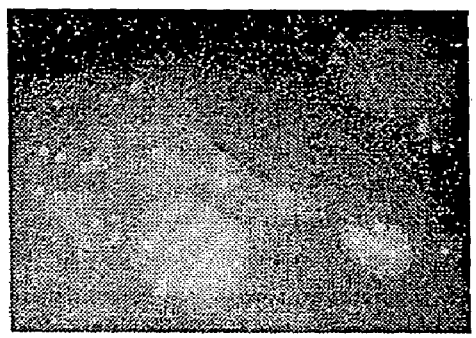
FIGS. 2A-2B demonstrate the expression of the mammalian expression vector pCR®3.1-Uni as control (FIG. 2A) and the plasmid containing the full length human ASMC-MR cDNA (FIG. 2B) in bovine airway smooth muscle cells. Final magnification is ×625.
Figure 2B:
Figure 2B:
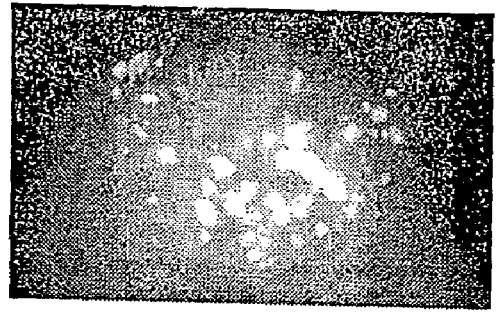

Expression of Human Airway Smooth Muscle Cell Mannose Receptor (huASMC-MR) cDNA Plasmid in Bovine Airway Smooth Muscle Cells A full length human cDNA clone was reconstructed and cloned into mammalian expression vector pCR®3.1-Uni under the control of CMV promoter. The mannose receptor on airway smooth muscle cells expression plasmid was transfected into bovine airway smooth muscle cells cells. Indirect immunofluorescence with a monoclonal antibody $mAb_{15-2-2}$ (Barrett-Bergshoeff et al., 1997) directed against Mø-MR demonstrated that the expressed mannose receptor on airway smooth muscle cells is predominantly localized to endosomes as indicated by punctate cytoplasmic signal (FIGS. 2A-2B).

After transfection with the full length human airway smooth muscle cell mannose receptor cDNA containing plasmid, 61% of the cells (1076/1747 compared to 57/1718 cells sorted in the vector control) showed an increase in fluorescence intensity due to binding of FITC-ManBSA but not due to binding of FITC-galactoseBSA (GalBSA) (data not shown). A 76% increase over baseline β-galactosidase activity was observed in parallel experiments. Antisense human airway smooth muscle cell mannose receptor morpholino DNA oligonucleotides (M-oligos, 25 mer, 5 μM) delivered by the scrape method inhibited b hexosaminidase-induced mitogenesis in bovine ASMC by 37% compared to no inhibition by sense M-oligos (data not shown). Ethoxylated polyethylenimine (EPEI) delivery system was cytotoxic beyond 3 μl/ml, limiting the concentration of antisense M-oligo delivery to the cells.

EXAMPLE 3 b Hexosaminidase-Induced Airway Smooth Muscle Cell Growth in vivo

Figure 3A:
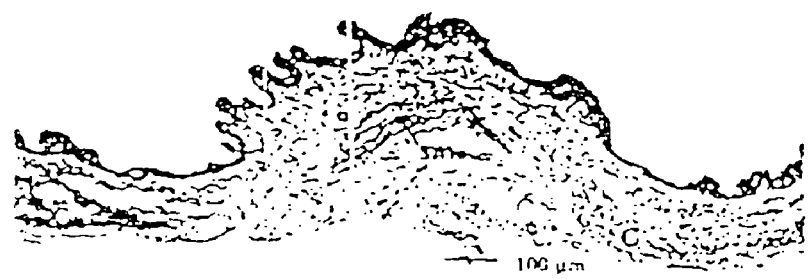
FIGS. 3A-3E demonstrate the effect of b hexosaminidases (Hex)-induced airway smooth muscle growth in Sprague-Dawley rats.
Figure 3B:
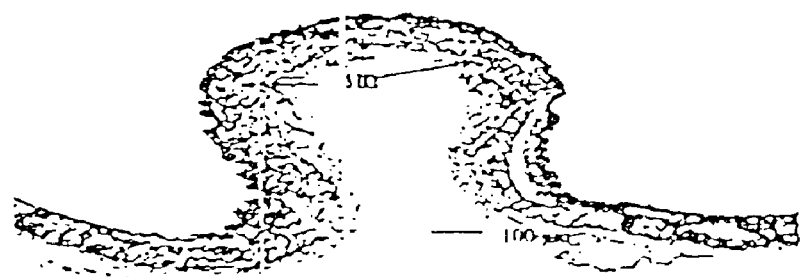
Figure 3C:
Figure 3D:
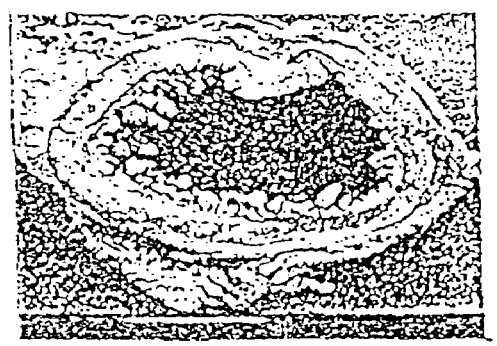
Figure 3E:

To examine the effect of b hexosaminidase on airway smooth muscle growth in vivo, a rat model was chosen for surgical implantation of mini-osmotic pumps. Subcutaneous pocket and tunnel were made in anesthetized rats. Pumps (ALZET, model 2002) were filled with either human placental b hexosaminidase of 1 mg/200 μl infused at 0.5 μl/hr (FIGS. 3B & 3D) or vehicle (5% glycerol in saline) (FIGS. 3A & 3C). The pumps were attached to 3" PE-10 catheters with end obliteration and side pores. The catheter was placed along the trachea. After completion of a 14-day infusion, the rats were sacrificed for histopathological examination in 4% paraformaldehyde fixed paraffin sections. FIG. 3E is a higher magnification of the trachealis muscle area marked by an arrow in FIG. 3B. Experiments were set in duplicate.

Figure 4:
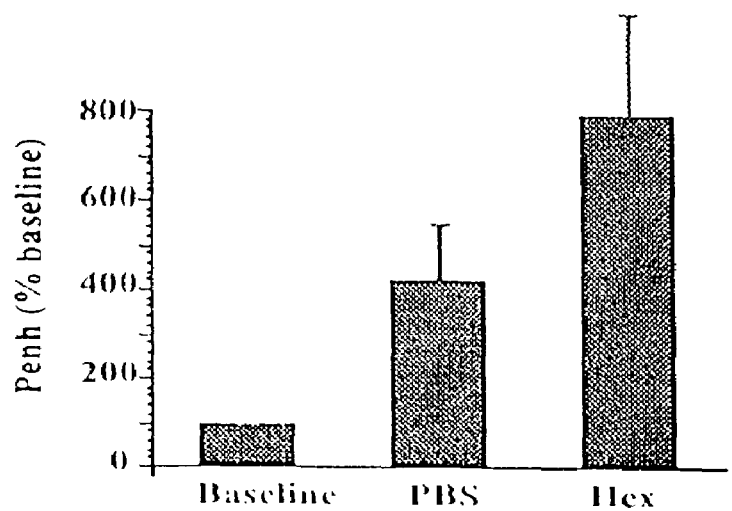

Aerosolized b hexosaminidase (Hex) increased airway hyperreactivity in naive wild type FVB/N mice (FIG. 4). Six week old FVB/N mice were treated with aerosolized human Hex A (1 mg) or vehicle (PBS) every other day for 2 weeks. On day 15, lung physiology was non-invasively assessed by methacholine (Mch) challenge and changes in pulmonary resistance (pause enhancement, Penh).

EXAMPLE 4

Comparing Mitogenic Effects of b Hexosaminidase with Other Growth Factors in Human Airway Smooth Muscle Cells Human airway smooth muscle cells (passage #5) in 24 well plates were starved for 18 h in 0.1% FBS containing medium. Cells were stimulated with Hex A (50 nM), PDGF (0.1 nM), EGF (100 nM), bFGF (5 nM), thrombin (Thr, 1 unit/ml), FBS (5% vol/vol), or vehicle (V; PBS for Hex; 0.1% BSA in 4 mM HCl for PDGF; 0.1% BSA for EGF and bFGF; unstimulated for Thr and FBS). Viable cell numbers were assessed by MTT assays after 42 h stimulation. The mitogenic effect of Hex A was comparable to that of PDGF and fetal bovine serum (FBS, 5% vol/vol) in serum-starved human airway smooth muscle cells (FIG. 5). However, after repeated passages, the human airway smooth muscle cells from the same batch (p10) responded poorly to Hex A, PDGF and thrombin. Experiments were repeated three times.

EXAMPLE 5

Airway Smooth Muscle Cell Mannose Receptor Transgenic Mouse Model

A smooth muscle specific ASM-MR transgenic (Tg) mouse model system using the SM22 gene promoter in collaboration with Dr. Alessandra d'Azzo (Member, St. Jude Children's Research Hospital, SJCRH, Memphis, Tenn.) was developed. The smooth muscle specific SM22 gene is highly expressed in lung and its gene expression is sustained in proliferating smooth muscle cells. Murine SM22α promotor region was isolated from mouse genomic DNA, amplified by PCR as described (Solway et al., 1995). The Tg construct contains the SM22 gene promotor, human airway smooth muscle cell mannose receptor cDNA in plasmid pCR3.1 Uni and a fragment containing β-globin intron.

The linearized construct was microinjected according to standard transgenic technique. Donor eggs were prepared from FVB/N mice because of the prominence of their embryo pronuclei and their strength to withstand injection, leading to a higher success rate. The FVB/N strain has been used to generate a lung-specific transforming growth factor α transgenic mice.

To construct the SM22 alpha/ASM-MR transgene, sense and anti-sense oligo nucleotide primers were designed based on the sequence of the SM22 alpha gene (5' region and exon 1; 3892 bp) (Accession No. U36589). Ind III sites were added to the 5' end of both primers for cloning purposes. The primers were used to generate a 502-bp fragment containing the 445-bp SM22 alpha promoter including exon 1 by PCR on genomic mouse DNA.

The promoter fragment was ligated 5' of full length coding region of ASM-MR cDNA (4,537 bp) in plasmid pCR 3.1 Uni and a fragment containing β-globin intron and polyadenylation signal (1.2 kb) was ligated 3' of ASM-MR cDNA. The 6.2 kb transgene fragment was excised with restriction endonuclease Pme I and used to generate transgenic mice in the FVR/NJ strain (FIG. 6A).

Three transgenic founders (F) were identified by tail-Southern blots of Hind III-digested DNA probed with a 1-kb fragment of the ASM-MR gene which recognizes an ~4.3 kb diagnostic band. The transgenic founders were confirmed by PCR analysis using ASM-MR oligonucleotide primers, amplifying an ~600 bp diagnostic band (FIG. 6B). Three available transgenic founders were analyzed to determine the influence of transgene integration and copy numbers on transgene expression. Transgenic founders carrying different copy numbers of the transgene were evaluated compared to littermate controls not expressing Tg(−).

EXAMPLE 6

OVA Sensitization and Airway Challenge

Groups of human ASM-MR Tg(+) or Tg(−) F2 generation littermate mice, ages 6-8 weeks, (four mice per group per experiment) are immunized by i.p. injection of ovalbumin (20 μg, grade V) emusified in 2.25 mg of aluminum hydroxide (Imject®-Alum; Pierce, Rockford, Ill.) on days 0, 14 and 21. Mice are challenged for 20 min via the airway with 1% ovalbumin in saline on days 28-30 using an ultrasonic nebulizer (Aerosonic ultrasonic nebulizer; DeVilbiss, Sommerset, Pa.). Control mice in both the Tg group and the littermate control group receive ovalbumin challenge alone without immunization, i.e., Alum alone via i.p. injection. Experiments are repeated 6 times on the following groups: Group 1: Littermate control+ovalbumin challenge; Group 2: Littermate control+ovalbumin sensitization+ovalbumin challenge; Group 3: ASM-MR Tg mice+ovalbumin challenge; Group 4: ASM-MR Tg mice+ovalbumin sensitization+ovalbumin challenge.

Airway hyper-reactivity is measured as follows. Twenty four hours after ovalbumin challenge on day 31, airway responsiveness to inhaled methacholine (MCh) is measured in conscious, spontaneously breathing animals by barometric plethysmography (Buxco, Troy, N.Y.). Mice are challenged with aerosolized saline or escalating doses of methacholine, e.g., 2.5-25 mg/ml in 1 ml, for 3 min and readings are taken and averaged for 5 min following each nebulization (FIG. 7). Enhanced pause (Penh) is measured using the software provided by the manufacturer.

Immediately after measuring MCh responsiveness, animals are anesthetized with Ketamine/Xylazine at 50/50 mg/kg and lungs are lavaged once via tracheal tube with 1 ml phosphate buffered saline (PBS, 37° C.). The broncho alveolar lavage_fluid is analyzed for Hex activity and differential cell count. Hex activity in broncho alveolar lavage_fluids is 262±33 μmoles/hr in immunized mice versus 92±12 in non-immunized mice.

EXAMPLE 7

Inhibition of Hex A-induced Mitogenesis by Mannan

Mannan, a polymer of mannose, is a specific mannose receptor blocker. Hex A-induced mitogenesis was inhibited by mannan in a concentration dependent manner in bovine and human airway smooth muscle cells. The specificity of mannan is demonstrated by its lack of inhibitory effect on PDGF-induced mitogenesis in human airway smooth muscle cells (FIG. 8).

Human airway smooth muscle cells in 24-well plates were starved for 18h in medium containing 0.1% FBS. Mannan in concentrations ranging from 0.1-1 mg/ml (Sigma) was added to the cells 30 min prior to the addition of 50 nM Hex A, 0.1 nM PDGF or vehicle (PBS for Hex or 0.1% BSA in 4 mM HCl for PDGF). Viable cell numbers were assessed by MTT assays after 42h stimulation. Experiments were repeated three times (FIG. 8).

EXAMPLE 8

Aerosolized Yeast Mannan Blocks Airway Hyper-Reactivity in OVA-Sensitized Murine Allergic Asthma Model Wild type FVB/N mice, ages 6-8 weeks, were immunized with ovalbumin (20 µg in Imject®-Alum, i.p.) on days 0, 14, 21 as described in Example 6. Non-immunized mice received i.p. injection of Alum only. Thirty minutes before each of the three ovalbumin challenges on days 28-30, the mice were pretreated via aerosol with 100 or 300 mg yeast mannan in 2 ml dH$_2$O or 5 EU *E. Coli* endotoxin (Sigma Chemical Co., St Louis, Mo.) in 2 ml saline. Experiments were performed in quadruplicate and repeated four times.

Measurements of airway hyper-reactivity (AHR) and broncho alveolar lavage were performed on day 31. Parallel experiments for sequential measurements of AHR were performed on days 31, 35, 38, and 45, that is, 1, 4, 7 and 14 days post the last dose of yeast mannan. Histopathology and immunohistology were performed on lungs and airways.

Methacholine sensitivity and reactivity were measured by Penh parameter in spontaneously breathing animals on day 31 (FIG. 9). Endotoxin at the given dosage did not inhibit OVA-induced airway hyper-reactivity. Mannan did not induce Hex secretion but inhibited TNFα secretion (85-100% inhibition) in BAL fluids. Endotoxin level of mannan was <2 EU/ml. This inhibitory effect was sustained for at least four days and the treated mice remained healthy and active for the duration of observation (3 weeks).

FIGS. 10-11 show mannan from *Saccharomyces cerevisiae* protects airway epithelium. FIG. 12 shows mannan from *Saccharomyces cerevisiae* inhibits cellular infiltration.

EXAMPLE 9

Comparison of Mannan with Other Chronic Asthma Therapeutics

On day 31, ovalbumin-sensititized and OVA-challenged mice are challenged as described above with 1) budesonide at 0.25-0.5 mg via aerosol 30 min prior to each of the ovalbumin challenges and 2) montelukast at 10 mg/kg via gavage feeding one day prior to the ovalbumin challenge and 4 h before each ovalbumin challenge on days 28-30. Experiments are set in quadruplicate and repeated four times.

The effect of mannan on cytokine profile in broncho alveolar lavage fluids can be assessed by cytokine array (TranSignal RayBio mouse cytokine antibody arrays, Panomics, Redwood City, Calif.) according to manufacturer's instructions. Selected cytokine levels, such as TNFα, IL-8 and other relevant cytokines in broncho alveolar lavage fluids can also be analyzed by Quantikine murine ELISA system (R & D systems, Minneapolis, Minn.) following manufacturer's instructions. Alternatively, cytokine measurements are performed by using Luminex (Fan and Mustafa, 2002).

Any patents or publications mentioned in this specification are indicative of the levels of those skilled in the art to which the invention pertains. Further, these patents and publications are incorporated by reference herein to the same extent as if each individual publication was incorporated specifically and individually by reference.

The following references are cited herein:

Barrett-Bergshoeff et al., Monoclonal antibodies against the human mannose receptor that inhibit the binding of tissue-type plasminogen activator. *Thromb Haemost.* 77:718-24 (1997).

Fan and Mustafa, Adenosine-mediated bronchoconstriction and lung inflammation in an allergic mouse model. *Pul. Pharm. Ther.* 15:147-155 (2002).

Leigh et al., Dysfunction and remodeling of the mouse airway persist after resolution of acute allergen-induced airway inflammation. *Am. J Respir. Cell Mol. Biol.* 27:526-535 (2002).

Lew et al., A mannose receptor mediates mannosyl-rich glycoprotein-induced mitogenesis in bovine airway smooth muscle cells. *J Clin. Invest.* 94:1855-1863 (1994).

Lew et al., The role of endogenously derived leukotrienes in the regulation of lysosomal enzyme expression in macrophages exposed to β-1,3-glucan. *J Leuk. Biol.* 49:266-276 (1991).

Sheikh et al., Endo180, an endocytic recycling glycoprotein related to the macrophage mannose receptor is expressed on fibroblasts, endothelial cells and macrophages and functions as a lectin receptor. *J Cell Sci.* 111:1021-1032 (2000).

Solway et al., Structure and expression of a smooth muscle cell-specific gene, SM22 alpha. *J Biol. Chem.* 270:13460-9 (1995).

What is claimed is:

1. A method for treating asthma in an individual in need of such treatment, comprising the step of:

administering a pharmacologically effective amount of a mannose receptor blocker consisting of yeast-derived mannan to the individual.

2. The method of claim 1, wherein the yeast is *Saccharomyces cerevisiae*.

3. The method of claim 1, wherein the mannose receptor is airway smooth muscle cell mannose receptor.

4. The method of claim 1, wherein blocking the mannose receptor inhibits onset of airway smooth muscle cell proliferation.

5. The method of claim 1, wherein the airway disease exhibits inflammation of the airway, airway hyperreactivity or a combination thereof.

6. The method of claim 1, wherein the mannose receptor blocker is administered via a nebulizer or via an inhaler.

7. A method for reducing airway smooth muscle mass in an individual with asthma in need of such treatment, comprising the step of:

administering a pharmacologically effective amount of an airway smooth muscle cell mannose receptor blocker consisting of yeast-derived mannan to the individual.

8. The method of claim 7, wherein the yeast is *Saccharomyces cerevisiae*.

9. The method of claim 7, wherein the mannose receptor blocker is administered via a nebulizer or via an inhaler.

* * * * *